(12) United States Patent
Aguirre et al.

(10) Patent No.: US 8,556,919 B2
(45) Date of Patent: *Oct. 15, 2013

(54) DELIVERY SYSTEM FOR MAGNETIC ANASTOMOSIS DEVICE

(75) Inventors: Andres F. Aguirre, Burlington, NC (US); Nestor Chopita, La Plata Provincia de Buenos Aires (AR)

(73) Assignee: Cook Medical Technologies LLC, Bloomington, IN (US)

( * ) Notice: Subject to any disclaimer, the term of this patent is extended or adjusted under 35 U.S.C. 154(b) by 286 days.

This patent is subject to a terminal disclaimer.

(21) Appl. No.: 12/776,995

(22) Filed: May 10, 2010

(65) Prior Publication Data

US 2010/0292729 A1  Nov. 18, 2010

Related U.S. Application Data

(60) Provisional application No. 61/178,674, filed on May 15, 2009.

(51) Int. Cl.
*A61B 17/03* (2006.01)
(52) U.S. Cl.
USPC .............................. 606/153; 600/12
(58) Field of Classification Search
USPC ...................... 606/151, 153–156, 213; 600/12
See application file for complete search history.

(56) References Cited

U.S. PATENT DOCUMENTS

| | | | |
|---|---|---|---|
| 6,056,722 A | 5/2000 | Jayaraman | |
| 6,312,406 B1 | 11/2001 | Jayaraman | |
| 6,692,460 B1 | 2/2004 | Jayaraman | |
| 2005/0182429 A1 | 8/2005 | Yamanouchi | |
| 2005/0228412 A1* | 10/2005 | Surti | 606/153 |
| 2008/0208224 A1 | 8/2008 | Surti et al. | |
| 2009/0281557 A1* | 11/2009 | Sander et al. | 606/151 |
| 2010/0256659 A1* | 10/2010 | Aguirre et al. | 606/153 |

FOREIGN PATENT DOCUMENTS

| | | |
|---|---|---|
| CA | 2 387 068 A1 | 2/2002 |
| CA | 2 757 558 A1 | 10/2010 |
| EP | 1 493 391 A1 | 1/2005 |
| JP | 2003 235852 A | 8/2003 |
| WO | WO 99/13935 | 3/1999 |

OTHER PUBLICATIONS

Canadian Intellectual Property Office Examiner's Report for corresponding Canadian Patent Application No. 2,761,871, Dec. 11, 2012, 3p.

* cited by examiner

*Primary Examiner* — Julian W Woo
*Assistant Examiner* — Shaun L David
(74) *Attorney, Agent, or Firm* — Brinks Hofer Gilson & Lione

(57) ABSTRACT

A magnet delivery system for forming an anastomosis that comprises a wire guide; a catheter having a delivery portion for advancement into a visceral space, the delivery portion having a lumen extending at least partially therethrough and an expandable balloon for dilation and a lumen extending therethrough, a first port and a second port in communication with the lumen through which the wire guide is disposed; a magnet comprising a lumen therethrough wherein the magnet is removably secured to the delivery portion of the catheter between the first and second ports by disposing the wire guide through the lumen of the magnet, the first port and the second port.

8 Claims, 7 Drawing Sheets

DELIVERY SYSTEM FOR MAGNETIC ANASTOMOSIS DEVICE

RELATED APPLICATION

The present application claims the benefit of U.S. Provisional Application No. 61/178,674, filed on May 15, 2009, the entirety of which is hereby incorporated by reference.

TECHNICAL FIELD

The present invention relates to delivery devices useful in delivering magnetic anastomosis devices.

BACKGROUND

Magnetic anastomosis devices (MADs) are currently used to create a channel between two viscera for the purpose of redirecting bodily fluids. For example, intestinal contents or bile may be redirected in patients who have developed an obstruction of the bowel or bile duct due to such conditions as tumor, ulcer, inflammatory strictures or trauma. A magnetic anastomosis device is disclosed in U.S. Pat. No. 5,690,656, the disclosure of which is incorporated herein by reference in its entirety. Generally, the MAD includes first and second magnet assemblies comprising magnetic cores that are surrounded by thin metal rims. Due to the magnetic attraction between the two magnetic cores, the walls of two adjacent viscera may be sandwiched and compressed between the magnet assemblies, resulting in ischemic necrosis of the walls to produce an anastamosis between the two viscera. The viscera treated by MADs include the gall bladder, the common bile duct, the stomach, the duodenum, and the jejunum of the small intestine.

Historically, MADs have been delivered through surgical intervention such as laparotomy, which of course is invasive and carries its own risks. The exemplary self-centering MAD of U.S. Pat. No. 5,690,656 permit delivery of the device over a wire guide and through the oral cavity, and typically under fluoroscopy. Alternatively, delivery can be accomplished by simply swallowing the magnet assemblies of the MAD and using massage under fluoroscopy to center the two magnet assemblies. Finally, delivery of the magnet assemblies has occasionally been performed endoscopically with grasping forceps, which can be time consuming and difficult. Removal of the MAD is typically accomplished by allowing the magnet assemblies to pass through the gastrointestinal track naturally, or more typically, with a follow-up endoscopic procedure using grasping forceps. Unfortunately, the relatively large size of the magnet assemblies can make delivery and retrieval complicated. In fact, balloon dilation of bodily lumens is often required in order to deliver the magnet assemblies to the desired location. Likewise, the size of bodily lumens is often the limiting factor in the size of the magnet assemblies that can be delivered and deployed.

Certain MAD procedures utilizing a jejunal magnet require the magnet to be passed down the esophagus to the stomach, and then through the pylorus and into the jejunum. Because of the curved nature of the passages leading to the jejunum, the magnet often becomes dislodged from the delivery system during advancement and placement thereof. Passing the jejunal magnet through the pylorus may be further complicated by patients with gastric outlet obstruction.

A general procedure for implanting a jejunal magnet to form an anastomosis can involve delivering a wire guide to the organ to be treated through an endoscope, dilating a stricture in the organ using an inflatable balloon, removing the balloon, and then delivering a new catheter to deliver the magnet.

BRIEF SUMMARY

Herein provided is a magnet delivery system for forming an anastomosis in a visceral space where an expandable balloon does not have to be removed before the jejunal magnet is placed. The delivery system comprises a wire guide, a catheter, and a magnet. The catheter has a delivery portion for advancement into the space. This delivery portion has an expandable balloon for dilation and a lumen extending at least partially through the delivery portion, first port, and a second port through which the wire guide is disposed. The magnet comprises a lumen through which the wire guide is disposed. The magnet is removably secured to the delivery portion of the catheter between the proximal and second ports by disposing the wire guide through the lumen of the magnet, the first port and the second port.

Also provided is a method for delivering a jejunal magnet for forming an anastomosis between two bodily walls. The delivery system provided herein is introduced into a bodily organ, such as any of the viscera. The balloon is expanded to dilate a portion of the bodily organ to be treated. The magnet, which is on the delivery portion of the catheter, is positioned adjacent the wall of a first organ. To deliver the magnet, the wire guide is withdrawn from the lumen of the magnet.

Also provided is a system having a delivery portion further comprising an additional first port, an additional second port, and an additional magnet that also comprises a lumen therethrough. This magnet is located between the additional first and second ports. The wire guide is placed through the lumen of the additional magnet such that it can be withdrawn later to deliver the magnet. There can be a single wire or separate wires. Such systems may allow the delivery of two magnets during one procedure.

The delivery system can be used in tandem with a second magnet delivery system as previously described. This second magnet delivery system may be used to position a second magnet adjacent the wall of a second organ such that it will be attracted to the first magnet placed adjacent to the wall of the first organ.

As described herein, the magnet is firmly attached to the delivery catheter and the likelihood of the magnet becoming dislodged during the procedure is minimized. The system described herein makes it possible to push the magnet through a gastric outlet obstruction.

DETAILED DESCRIPTION OF THE DRAWINGS AND THE PRESENTLY PREFERRED EMBODIMENTS

The term "prosthesis" means any replacement for a body part or for a function of that body part or any device that enhances or adds functionality to a physiological system.

The term "catheter" generally means a medical device comprising an elongate shaft having a lumen extending at least partially therethrough, including balloon catheters, guide catheters, and delivery catheters. An example of a catheter includes the Cook Medical Fusion™ Biliary Dilation Catheter (FS-BDC).

Figure 1:
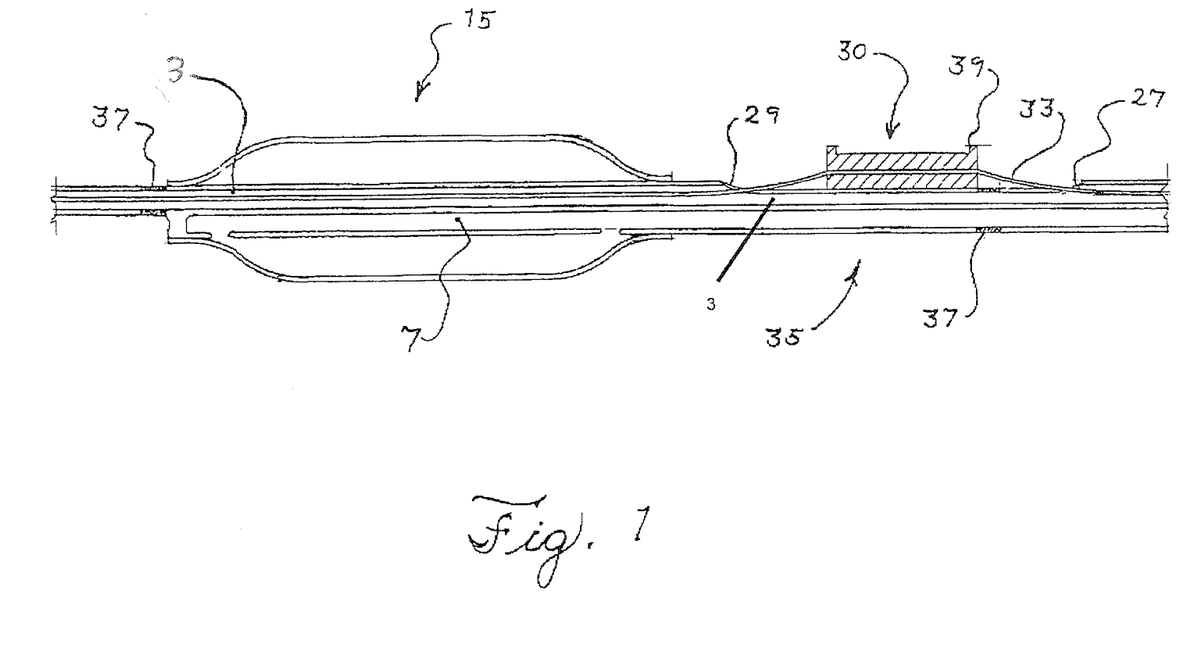
FIG. 1 is a cross-sectional view of a delivery portion of the catheter.

The magnet delivery system uses a catheter 35, a wire guide 33, and an expandable balloon 15 to deliver a jejunal magnet 30. FIG. 1 provides a cross-sectional view of the delivery portion of the catheter 35. The expandable balloon 15 is on the distal end of catheter 35 and is also distal to the magnet 30. The balloon 15 precedes the magnet 30 during implantation so that it may dilate any strictures in the organ to be treated. Once dilation has occurred, the magnet 30 can be advanced to the wall of the organ to be treated. FIG. 1 shows that the path of the wire guide 33 through the lumen of the magnet 30, the first 27 and second 29 ports, and a first lumen 3 of the catheter 35. The catheter 35 has a second lumen 7 that is in fluid communication with the interior of the expandable balloon 15. Expandable balloon 15 can be non-compliant with a predetermined shape and fabricated from polyethylene, polyethylene terephthalate (PET), or polyamides.

Figure 2:
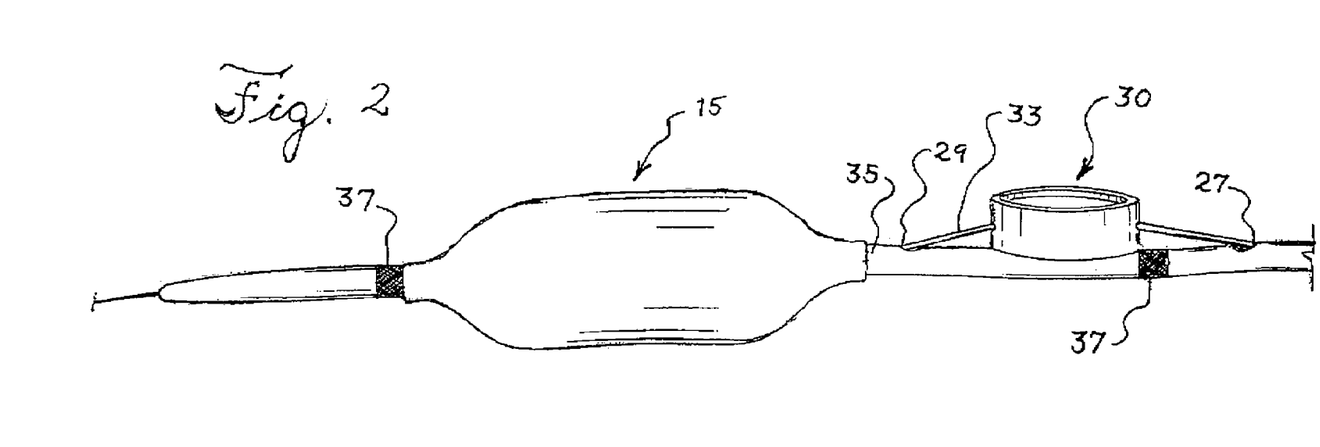
FIG. 2 is a perspective view of a delivery system described herein.

As seen in FIG. 2, the catheter 35 has two ports, a first port 27 and a second port 29 through which the wire guide 33 is placed. Suitable wire guides can include the Cook Medical Tracer Hybrid® Wire Guides (HYB-48015). The first 27 and second 29 ports are sufficiently spaced apart to accommodate the magnet 30 between them. The ports 27, 29 are about 35 mm to about 70 mm apart or any combination or subcombination of ranges therein. In the particular embodiment illustrated, the ports 27, 29 can be spaced about 60 mm apart. The preferred distance will range across standard sizes used in the field. Magnets between about 10 mm and 20 mm in diameter or any combination or subcombination of ranges therein may be accommodated, although a magnet about 14 mm in diameter is illustrated. For other magnet sizes the location of the ports in the catheter lumen may be modified as required.

The magnet 30 shown has a general disc shape (i.e. having an axial height which is less than the outer diameter). Magnets that may be used in this delivery system can be circular, cubular, cylindrical, polygonal, oval or ovoid, square or the like. Numerous other shapes of the magnets may be readily envisioned by those skilled in the art. The magnet 30 may include a protective coating which may be formed of various materials such as polymers like Teflon® or Paralene® for protection of the magnetic core from the corrosive effects of digestive acids or other bodily fluids depending upon the bodily structure involved.

The magnet 30 has a lumen therethrough to accommodate the wire guide 33. The magnet 30 also comprises an annular edge 39 along the magnet's perimeter. The edge 39 is slightly raised above the center of the magnet 30 such that it forms a basin 32 to accommodate or mate with a second magnet (as described below). In particular, when the magnet 30 is delivered, this edge 39 contacts the wall of the viscera and helps to initiate the ischemic necrosis of the tissue captured between the magnet 30 and a mated second magnet. A radiopaque marker 37 is placed on the catheter in the vicinity of the magnet to mark the magnet location when viewed through fluoroscopy. A radiopaque marker can be placed underneath the magnet 30 on the catheter 35 to mark the location of the magnet when viewing the delivery system from the side.

Figure 3:
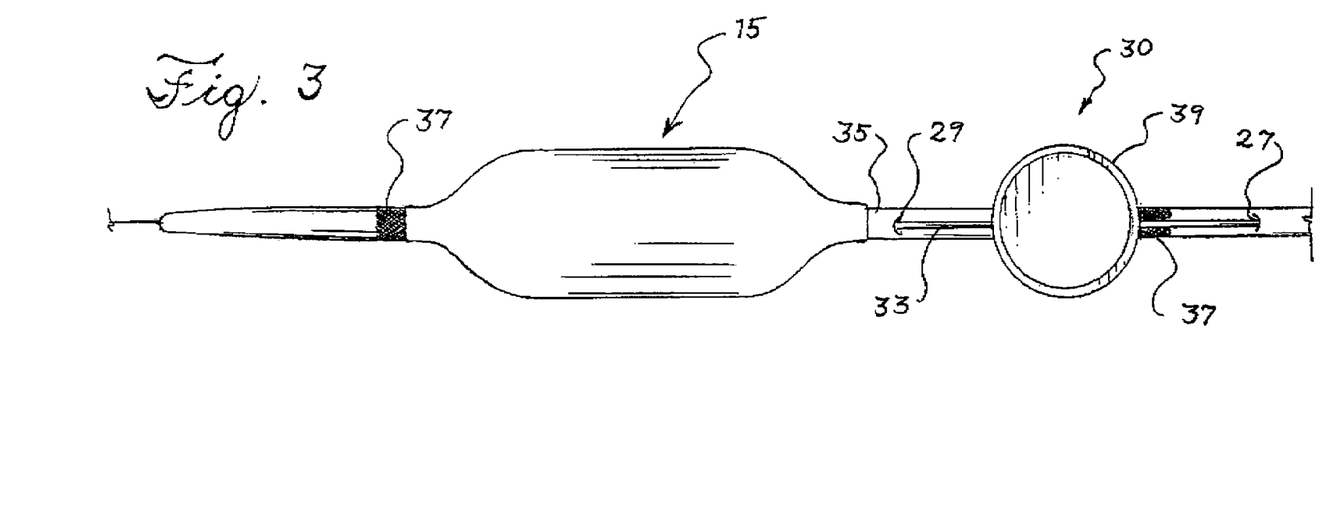
FIG. 3 is an overhead view of a delivery system.

The wire guide 33 holds the magnet 30 in place on the distal end of the catheter 35. In FIGS. 1 through 3, the wire guide 33 is shown protruding from the first port 27, going through the lumen of the magnet 30, and re-entering the catheter 35 at the second port 29. The wire guide 33 and the catheter 35 may include radiopaque markers 37 that permit tracking of the delivery system for accurate positioning of the magnet 30. It may be preferred that a radiopaque marker 37 be placed immediately distal to the magnet 30. The catheter 35 may be used alone or in conjunction with other wire guide cannulae for navigation of the bodily lumens and delivery of a magnet.

Figure 4:
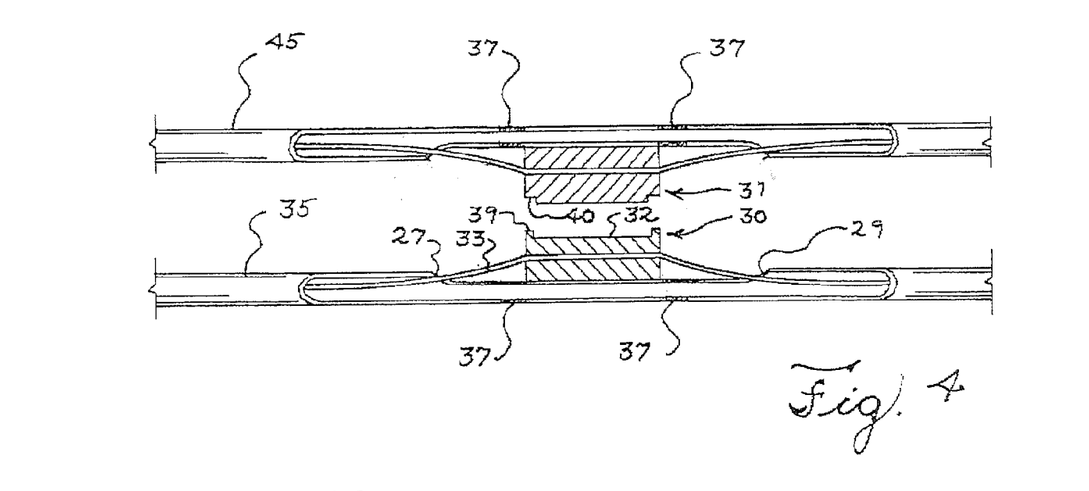
FIG. 4 is a perspective view of two delivery systems with complementary jejunal magnets.
Figure 9:
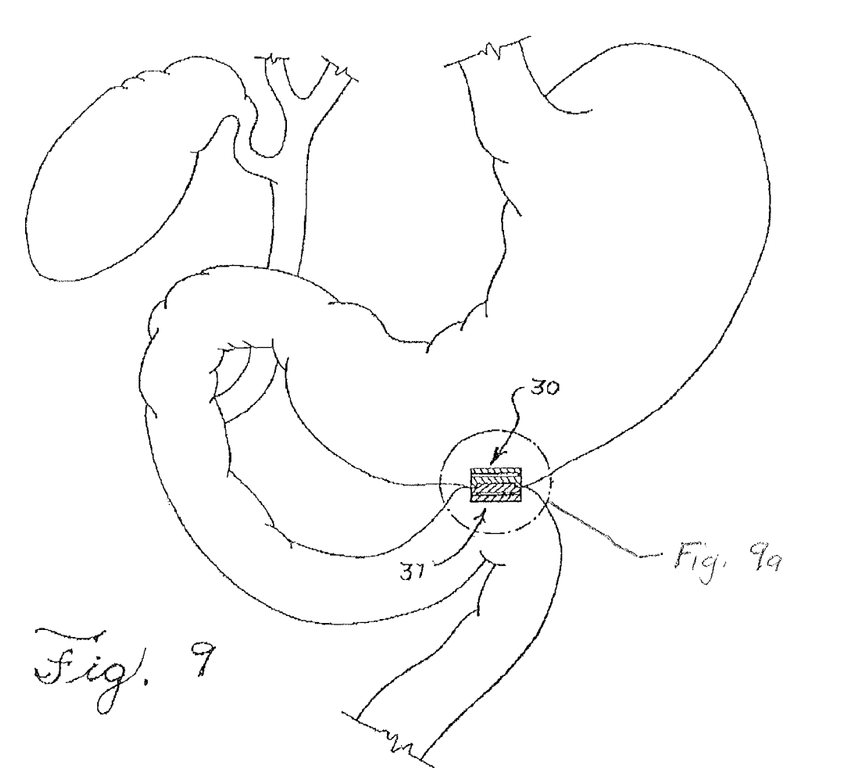
FIG. 9 schematically depicts two magnets compressing the walls of the stomach and the jejunum to facilitate a new anastamosis.
Figure 9A:
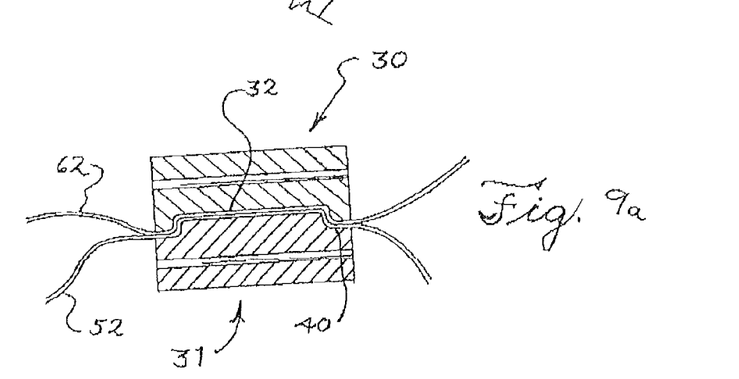
FIG. 9a is a cross-sectional view of two magnets compressing the walls of two internal bodily organs to facilitate a new anastamosis.

FIG. 4 shows two delivery systems where a second magnet 31 is affixed to a second catheter 45. The second magnet 31 has an annular recess 40 that is capable of mating with the annular edge 39 of the first magnet 30. FIG. 9a shows the walls 52, 62 of two viscera being compressed between magnets 30, 31. The edge 39 compresses the walls against the second magnet 31 to assist the ischemic necrosis. The second magnet 31 can also have an annular edge with a smaller diameter than the first magnet 30. When implanted and mated with the first magnet 30, the second magnet 31 can fit within the annular edge 39 of the first magnet 30.

Figure 5:
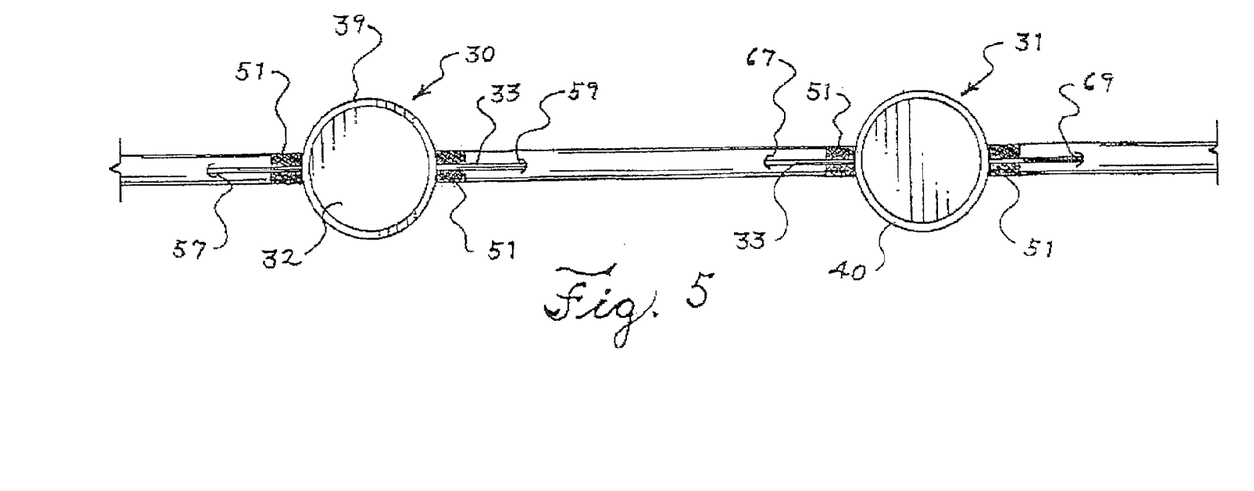
FIG. 5 is an overhead view of a dual delivery system.

FIG. 5 shows a system for the delivery of two magnets 30, 31. Such a system may be used as an efficient means of delivering multiple magnets. Although two magnets 30, 31 are shown, more than two magnets can be coupled to a catheter in the fashion described herein. The catheter has four ports in total: first 57 and second 67 proximal ports and first 59 and second 69 distal ports. First magnet 30 is held between first port 57 and second port 59 with wire guide 33. The additional magnet 31 is constrained between first port 67 and second port 69 with wire guide 33. The first magnet 30 comprises an annular edge 39 with a basin 32. The annular recess 40 on the additional magnet 31 mates with the annular edge 39 of the first magnet 30 when both magnets are implanted. Two sets of radiopaque markers 51 can be used with a second radiopaque marker 51 located distal to the second magnet 31. In general, the radiopaque markers 51 can be located on the delivery portion sufficient to guide an operator during the placement procedure. Methods for delivering both magnets using such a system are described further below.

Figure 6:
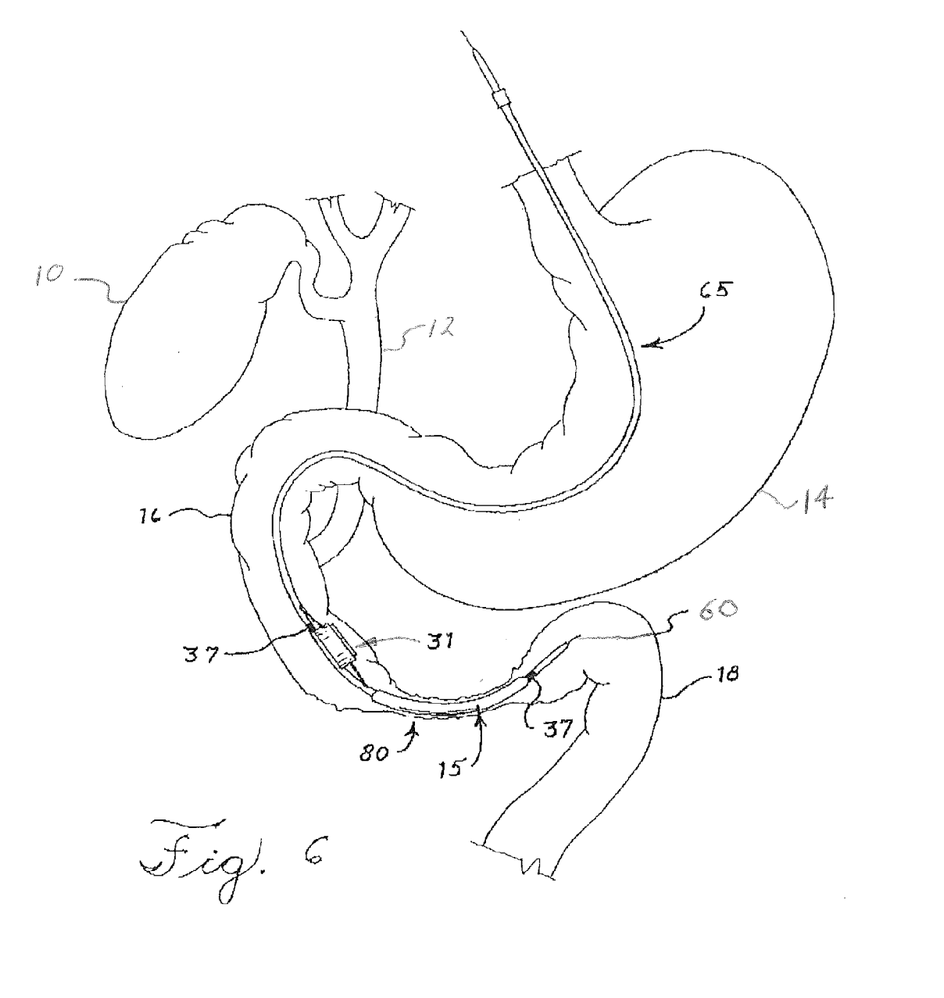
FIGS. 6 and 7 schematically depict a delivery system addressing a stricture in the jejunum.

It will be recognized by those skilled in the art that the magnetic anastamosis device employing the magnet assemblies described herein not only preserves the benefits of improving the time of the procedure to place the magnet, but further provides a small delivery configuration which may be easily located within the body for accurate delivery. The delivery systems described herein also provide for insertion of the magnets through natural orifices. As such, there is also a method for delivering the magnet assembly to a position for forming an anastamosis between two viscera. FIG. 6 shows the relative positions of several viscera in the abdominal cavity, including the gall bladder 10, the common bile duct 12, the stomach 14, the duodenum 16, and the jejunum 18 of the small intestine. Although not shown, the delivery system described herein can also be used to implant anastamosis-forming magnets in the colon for possible use in gastric bypass procedures. The delivery system described herein can be used, for example, to create an anastomosis between the stomach 14 and the jejunum 18 of the small intestine. The delivery system can also be used as a part of procedure where forceps are used to place one of the magnets.

Figure 7:
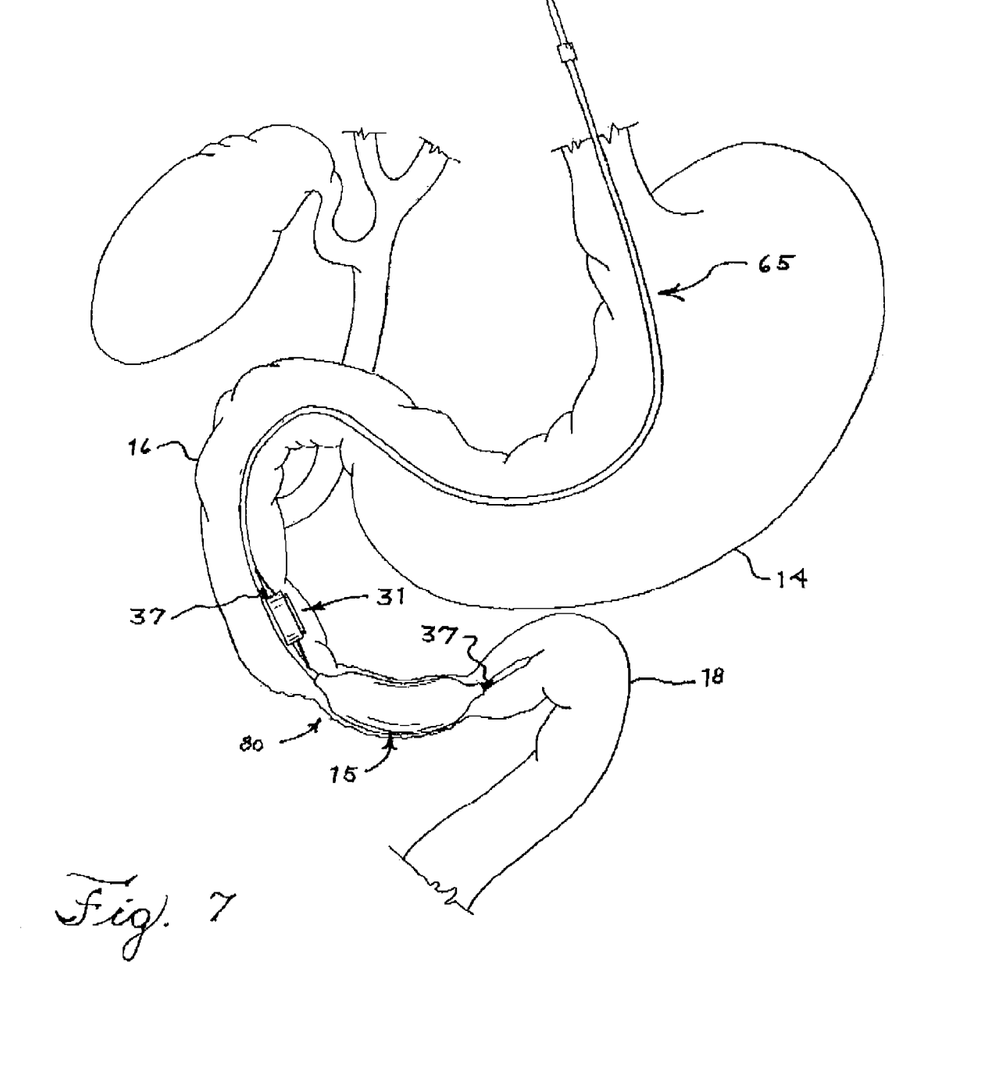

The method for delivering a jejunal magnet to form an anastomosis comprises introducing the delivery system 65 into an endoluminal vessel. In FIG. 6, a delivery device 35 as described herein is shown being advanced toward a stricture 80 in the jejunum 18. The balloon 15 is expanded to dilate the stricture 80 so that the catheter 35 can be advanced to the selected treatment site. The expanded balloon 15 is shown in FIG. 7 compacting the walls of the jejunum to make way for the magnet 31.

The delivery of magnet 31 follows once the wire guide 60 has been positioned adjacent the wall of a first viscus, the jejunum 18, in FIG. 6. The magnet 31 is placed on a dilation catheter 35 as shown in FIG. 1 and held in place on the catheter 35 by the wire guide 33. The wire guide 33 is loaded through the catheter 35, passing through second port 29 in the catheter 35 lumen, through the lumen of the magnet 30, and then reentering the catheter 35 lumen through first port 27. Using the radiopaque markers 37 as a guide, the catheter 35 is advanced such that the magnet 31 is placed adjacent to the wall of the jejunum 18 as shown in FIG. 8.

Figure 8:
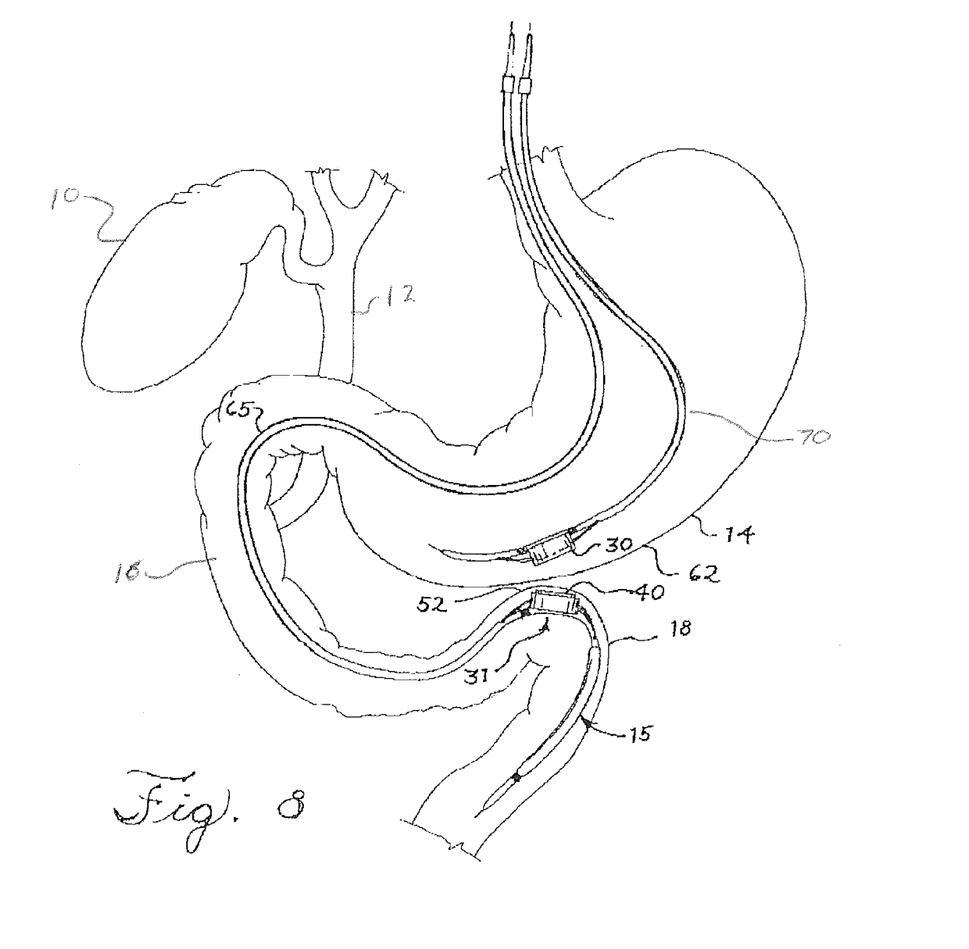
FIG. 8 schematically depicts two magnet assemblies implanted in the body for forming a magnetic anastamosis device in accordance with the present description.

The delivery system 65 with magnet 31 remains in position as a second delivery system 70 is introduced into the stomach 14 as shown in FIG. 8. Magnet 30 is positioned adjacent the wall of the stomach 14 that borders the jejunum 18 near the location of magnet 31. To release magnet 31, the operator removes the wire guide 33 and then the catheter 35. Magnets 30, 31 are released so that the magnetic forces attract the magnets together, compressing the walls 52, 62 together of the jejunum 18 and the stomach 14 as seen in FIG. 9. FIG. 9a is a close up view of magnets 30 and 31 compressing the walls 52 and 62.

The attraction forces exerted between the magnets 30, 31 are high enough so that in the event that the catheter 35 is caught between the two magnets 30, 31 after the placement of magnet 30, the catheter 35 may be removed and the magnets 30, 31 will remain together. The radiopaque markers 37 can be used as a guide to help position the magnet 31 in the correct orientation under fluoroscopy. A radiopaque marker 37 may be located at the proximal edge of the magnet as exemplified in FIG. 1.

Once the necrosis of the walls of the stomach and the jejunum is complete, an anastomosis is formed. The magnets 30, 31 can then pass through the body naturally or can be removed by means such as laparotic removal, endoscopic removal, or other procedure.

The delivery system shown in FIG. 5 can be used to deliver two magnets using one catheter. Magnet 31 can be delivered first to a first location to be treated by retracting the guidewire 33 sufficiently to release the magnet 31. The delivery portion of the catheter can then be positioned in a second location where magnet 30 can be released by further retracting the guidewire 33 from the lumen of the magnet 30. The magnets 30, 31 can be maneuvered to mate with one another by massage under fluoroscopy or by grasping forceps through laparoscopic surgery. Once mated, as shown in FIG. 9a, the ischemic necrosis process can begin on the walls of the two viscera being treated.

The foregoing description of has been presented for purposes of illustration and description. It is not intended to be exhaustive or to limit the delivery systems and methods disclosed. Numerous modifications or variations are possible in light of the above teachings. The delivery systems and methods disclosed were chosen and described to provide the best illustration of the principles of the delivery systems and methods and their practical application to thereby enable one of ordinary skill in the art to utilize the delivery systems and methods in various embodiments and with various modifications as are suited to the particular use contemplated. All such modifications and variations are within the scope of the delivery systems and methods as determined by the appended claims when interpreted in accordance with the breadth to which they are fairly, legally, and equitably entitled.

The invention claimed is:

1. A magnet delivery system for forming an anastomosis, the delivery system comprising:
   a wire guide;
   a catheter comprising an elongate shaft having a delivery portion for advancement into a visceral space, the delivery portion having an expandable balloon configured for dilation attached about the shaft, a lumen extending through the shaft of the delivery portion, the lumen traversing an interior of the expandable balloon, and a first port and a second port in communication with the lumen through which the wire guide is disposed;
   a magnet comprising a lumen therethrough, wherein the magnet is removably secured to the delivery portion of the catheter between the first and second ports by disposing the wire guide through the lumen of the magnet, the first port and the second port; and
   wherein the expandable balloon is distal to both the first port and the second port.

2. The magnet delivery system of claim 1 where the magnet has a disc shape.

3. The magnet delivery system of claim 1 where the magnet further comprises an annular edge for placement against the wall of a bodily organ.

4. The magnet delivery system of claim 1 where the magnet further comprises an annular recess for placement against the wall of a bodily organ.

5. The magnet delivery system of claim 1 where the delivery portion further comprises an additional first port, an additional second port, and an additional magnet comprising a lumen therethrough, the additional magnet being removably secured to the delivery portion of the catheter between the additional first and second ports, wherein the additional first and second ports are each disposed proximally of the first port, the second port, and the expandable balloon.

6. The magnet delivery system of claim 5 where the wire guide is placed through the lumen of the additional magnet, the additional first port, and the additional second port to secure the additional magnet to the delivery portion.

7. The magnet delivery system of claim 5 where the magnet further comprises one of an annular edge or an annular recess for placement against the wall of a bodily organ and the additional magnet further comprises the other of the annular edge or the annular recess for placement against the wall of a bodily organ, the annular edge being configured to mate with the annular recess.

8. The magnet delivery system of claim 1 further comprising a radiopaque marker located on the delivery portion of the catheter, where the radiopaque marker is proximate the magnet.

* * * * *